United States Patent [19]

Kessels

[11] Patent Number: 5,210,288
[45] Date of Patent: May 11, 1993

[54] PROCESS FOR THE PREPARATION OF D-(−)-4-HYDROXYPHENYLGLYCINE AND L-(+)-4-HYDROXYPHENYLGLYCINE, STARTING FROM D.L.-4-HYDROXYPHENYLGLYCINE

[76] Inventor: Gerard Kessels, Apartado 294, 04630 Garrucha (Almeria), Spain

[21] Appl. No.: 669,488

[22] Filed: Mar. 14, 1991

[30] Foreign Application Priority Data

Mar. 21, 1990 [NL] Netherlands ............................ 9000653

[51] Int. Cl.$^5$ ...................... C07B 57/00; C07C 229/42
[52] U.S. Cl. ........................................ 562/401; 560/39; 562/444
[58] Field of Search .................... 562/401, 444; 560/39

[56] References Cited

U.S. PATENT DOCUMENTS 3,994,962 11/1976 Shirai et al. ......................... 562/444

*Primary Examiner*—Paul J. Killos
*Assistant Examiner*—B. Frazier
*Attorney, Agent, or Firm*—Kane, Dalsimer, Sullivan, Kurucz, Levy, Eisele and Richard

[57] ABSTRACT

The invention relates to a process for the preparation of D-(−)-4-hydroxyphenylglycine and L-(+)-4-hydroxyphenylglycine starting from D.L.-4-hydroxyphenylglycine. According to the invention the D.L.-4-hydroxyphenylglycine is dissolved in a suitable solvent or a mixture of solvents at an increased temperature, which solvent mixture comprises an organic solvent, $H_2SO_4$ and water. Then the solution obtained is cooled and to the cooled solution are added D-(−)-4-hydroxyphenylglycine sulphate inoculation crystals for crystallizing the D-(−)-4-hydroxyphenylglycine sulphate, followed by filtering of the formed crystals. For recovery of L-(+)-4-hydroxyphenylglycine sulphate remaining in the mother liquor, the mother liquor is heated, followed by addition of D.L.-4-hydroxyphenylglycine and a solution of $H_2SO_4$ and water. The resulting solution is cooled down, followed by addition of L-(+)-4-hydroxyphenylglycine sulphate inoculation crystals, from which mixture after further cooling the L-(+)-4-hydroxyphenylglycine sulphate crystallizes.

9 Claims, No Drawings

PROCESS FOR THE PREPARATION OF D-(−)-4-HYDROXYPHENYLGLYCINE AND L-(+)-4-HYDROXYPHENYLGLYCINE, STARTING FROM D.L.-4-HYDROXYPHENYLGLYCINE

STATE OF THE PRIOR ART

Both enantiomers of 4-hydroxyphenylglycine are important starting materials for the preparation of various medicines.

D-(−)-4-hydroxyphenylglycine is used for the preparation of antibiotics. For the production of the semi-synthetic penicillin, amoxycillin and the semi-synthetic cephalosperines cephahydroxyl and cephatrisine the D-(−)-4-hydroxyphenylglycine is an indispensable starting material.

L-(+)-4-hydroxyphenylglycine is the active ingredient of oxphenicine, a new medicine for the treatment of heart diseases.

There is an extensive prior art, which is represented by the following literature.

S. Yamada et al describe in Agrio.Biol.Chem. 43 (1979), p. 395, a process by which D.L.-4-hydroxyphenylglycine is split by means of (+)-3-bromocamphor-8-sulphonic acid. Disadvantages of this process are that (+)-3-bromocamphor-8-sulphonic acid is an expensive auxiliary material with a high molecular weight, which is moreover not completely stable, while the process provides only the D-(−)-enantiomer in pure form. There are known a number of chemical processes in which one starts from a derivative of D.L.-4-hydroxyphenylglycine and whereby one executes the resolution with an optically active auxiliary means. Processes of this type have been disclosed among others in the following patent specifications: U.S. Pat. No. 3,705,900; U.S. Pat. No. 3,796,748; U.S. Pat. No. 3,832,388; GB 1,314,739; DE 2,345,302 and BE 772,894.

All these processes have the disadvantages that a derivative of the D.L.-4-hydroxyphenylglycine must first be made by a chemical reaction, further the resolution is executed with a relatively expensive splitting means and then again with the use of a chemical reaction the derivative must be converted in the amino-acid.

Another disadvantage is that only the D(−)enantiomer is obtained. Many process steps are necessary for making and decomposing the derivatives and the recovery of valuable splitting means.

According to the processes described in the German patent application 2807286, Dutch patent application 7513551 and U.S. Pat. No. 3,517,023 derivatives of D.L.-4-hydroxyphenylglycine are optically selective partly hydrolyzed by an enzyme. Disadvantages of the processes are, that first a derivative must be made, whereas in abundance a chemical reaction must be executed in order to obtain the free amino acid. It is also a disadvantage that only the D(−)enantiomer can be prepared. Also an enzyme is necessary, which is neither stable nor inexpensive.

The processes described in the undermentioned patent specifications start from the starting material D.L.-5-(4-hydroxyphenyl)hydantoin: U.S. Pat. No. 4,211,840 and IT patent application 1,506,067.

With an optically selective enzyme an optically selective hydrolysis is executed, whereby only the D(−)enantiomer is obtained. Further still a chemical reaction is executed to obtain the free D(−)amino acid. Disadvantages of this process are among others that D.L.-5-(4-hydroxyphenyl)hydantoin is a more expensive starting material and has a substantially higher molecular weight than D.L.-4-hydroxyphenylglycine. Besides an enzyme must be made through a fermentation, whereby problems may arise by virus infections, through which the obtained enzyme is not of the required quality.

Likewise processes are known, whereby sulphonic acid salts of D.L.-4-hydroxyphenylglycine are split by a technique of preferential crystallization into both the D(−) and L(+) enantiomer. These processes have been disclosed among others in the following patent specifications: JP 1,532,151, British Patent No. 1532151 and European Patent Application Published under 070114.

In the processes described in these patent specifications an amount of inoculation crystals of the sulphonic acid salt of one of the enantiomers is added to a supersaturated solution of a sulphonic acid salt of D.L.-4-hydroxyphenylglycine. Now crystallization arises of the salt of the enantiomer which crystals have been added. These processes have in principle large advantages over the previously mentioned methods.

One starts from D.L.-4-hydroxyphenylglycine which forms spontaneously with the necessary sulphonic acid the salt in solution, while the sulphonic acid salt obtained of the obtained enantiomers may be converted very simply with alkali in an aqueous medium into the amino-acid. No complicated chemical reactions are necessary and neither is necessary an expensive optically active splitting means nor an optically selective enzyme.

However, the described processes are also connected to serious disadvantages, which make an industrial application difficult.

One works with supersaturated solutions, through which there is present constant danger that the enantiomer which is not desired starts to crystallize. The further the crystallization of the desired enantiomer advances, the greater the risk will be that the non-desired enantiomer crystallizes. By so doing the crystallized enantiomer is often not optically pure and should therefore be recrystallized. Also the productivity of the process is low. One needs relatively much inoculation material with respect to the amount of product, which may be crystallized and the yield of enantiomer per liter of the solution is not high.

Now the invention provides a process, whereby the above-mentioned disadvantages are successfully removed.

To this end the invention provides a process for the preparation of D-(−)-4-hydroxyphenylglycine and L-(+)-4-hydroxyphenylglycine starting from D.L.-4-hydroxyphenylglycine, characterized in that the D.L.-4-hydroxyphenylglycine is dissolved in a suitable solvent or a mixture of solvents at an increased temperature, which solvent mixture comprises an organic solvent, $H_2SO_4$ and water, after which the solution obtained is cooled and to the cooled solution are added D-(−)-4-hydroxyphenylglycine sulphate inoculation crystals for crystallizing the D-(−)-4-hydroxyphenylglycine sulphate, followed by filtering of the formed crystals, while for the recovery of L-(+)-4-hydroxyphenylglycine sulphate remaining in the mother liquor, the mother liquor is heated, followed by addition of D.L.-4-hydroxyphenylglycine and a solution of $H_2SO_4$ and water, after which the thus obtained solution is cooled down, followed by addition of L-(+)-4-hydroxyphenylglycine sulphate inoculation crystals, from which mixture after further cooling the L-(+)-4-hydroxyphenylglycine sulphate crystallizes; whereby one may also act reversely, that is first the L-(+)-4-hydroxyphenylglycine sulphate is crystallized and thereafter from the mother liquor the D-(−)-4-hydroxyphenylglycine sulphate and, if desired, from the formed sulphates the D-(−)-4-hydroxyphenylglycine and the L-(+)-4-hydroxyphenylglycine, respectively, may be recovered by hydrolysis.

The process according to the invention is a racemate splitting too, using the technique of preferential crystallization, however, on the understanding that a number of disadvantages of the previously mentioned preferential crystallizations are removed and an industrially proper executable process is obtained.

Use is made of the fact that the hydrosulphate of D.L.-4-hydroxyphenylglycine is very well soluble in diverse solvents, but not so the sulphate. One may so easily make a solution of the hydrosulphate at a somewhat higher temperature, however, on cooling down a part of the D.L.-4-hydroxyphenylglycine crystallizes as the sulphate. If, however, during cooling the inoculation is done with the sulphate of one of the enantiomers, then only the sulphate of this enantiomer crystallizes, whereas the hydrosulphate of the other enantiomer remains in solution. It is remarkable in this preferential crystallization that there is apparently no supersaturated solution of the other enantiomer present after crystallization of the enantiomer with which the inoculation was done, so that if after crystallization of the desired enantiomer the crystals formed are removed by filtration, no crystallization takes place in the residual mother liquor of the sulphate of the other enantiomer, neither after inoculation. It is supposed that the reason of this phenomenon could have been that when the sulphate crystallizes from the hydrosulphate an equivalent of sulphuric acid is liberated.

Thus during crystallization the solution grows richer in sulphuric acid, making it less easy to crystallize sulphate, that is from sulphate with sulphuric acid a hydrosulphate is formed.

This means that during crystallization of the sulphate of the desired enantiomer, the solubility of the other one relatively increases, through which no supersaturated solution arises.

The consequences of this phenomenon are far-reaching. In comparison with the known preferential crystallizations this new process has the large advantage that a real industrial process is obtained. One needs no longer to separate quickly the crystals of the desired enantiomer after the crystallization, for the mother liquor is not a supersaturated solution of the other enantiomer and there is no danger that an undesired crystallization arises, through which the optical purity of the product decreases. Also a much larger part of the desired enantiomer present in the solution can be crystallized in comparison with the known preferential crystallizations, while a relatively small amount of inoculation material need be used.

With respect to other kinds of racemate splittings the advantages are that no expensive optically active auxiliary means is used, no enzymes are necessary, no derivatives need be made of the D.L. compound, which should be decomposed after the resolution again.

According to the process of the invention per equivalent of 4-hydroxyphenylglycine 1 equivalent of sulphuric acid is used, while the obtained sulphate of the enantiomer can be converted in the free amino-acid by a simple hydrolysis with alkali or ammonia, whereby in the waste water of the racemate splitting process only one equivalent of sodium, potassium or ammonium-sulphate is present.

According to the present process first a warm solution is made of the hydrosulphate of D.L.-4-hydroxyphenylglycine in a solvent comprising between 0 and 30% of water. To this end the solvent containing the D.L.-4-hydroxyphenylglycine is heated to 40°-100° C. As solvents are used generally those solvents which are wholly or partially mixable with water, or mixtures of solvents. So there may be used carboxylic acids like formic acid and acetic acid, alcohols like methanol, ethanol, propanoles, butanoles and ethyleneglycol and ethyleneglycolmonoalkylethers, ketones like acetone and methylethylketone. An amount of water is added to obtain a proper formation of the hydrosulphate and a sufficient solubility. In substantially all solvents the sulphate of D.L.-4-hydroxyphenylglycine is not at all soluble without water. If one tries to make a solution without adding water, then the sulphate crystallizes directly during the addition of D.L.-4-hydroxyphenylglycine and sulphuric acid in the solvent.

It appears that the required water concentration is different for the diverse solvents.

So one may obtain with a few percents of water already a suitable solubility and a proper crystallization in, for instance, methanol, acetic acid and formic acid, whereas about 20% of water is necessary in isopropanol or glycolmonoethylether in order to obtain a sufficient solubility and a proper crystallization.

In practice it appears that the solvents in which the -4-hydroxyphenylglycine sulphate does dissolve properly, for instance, methanol, provide a faster crystallization, but that the optical purity of the obtained enantiomer is not always 100%, whereas, for instance, in the butanoles one can only work with low concentrations, but the crystallization proceeds slowly and the optical purity is high.

If a single solvent is taken, then acetone is used preferably as a solvent.

It has appeared that a mixture of, for instance, methanol and n-butanol exactly gives proper results.

As has been stated before, the addition of water has the function to obtain a sufficient solubility. However, one should not add so much water that two phases arise. This risk is there among others with the butanoles. In practice it appears that at a water content of 15-20% a proper crystallization may be had, while at a water content of more than 30% no good crystallization is obtained anymore. If once a solution is obtained of the D.L.-4-hydroxyphenylglycine hydrosulphate, then this solution is cooled down. During the cooling down a small amount of inoculation crystals of the sulphate of the enantiomer which is to be crystallized are added. Now crystallization of the desired enantiomer takes place.

Further the formed crystals may be separated from the mixture by, for example, filtration. It is not necessary, as is with the known preferential crystallizations, to separate very quickly the obtained crystals from the crystallization mixture. It appears that on waiting some hours after the crystallization, there is still no change in the obtained crystals. The crystallization mother liquor does not appear to be supersaturated.

With the known preferential crystallizations the crystallization mother liquor is supersaturated with the enantiomer which is not desired to be crystallized. If the obtained crystals are not quickly filtrated from the crystallization liquid crystallization arises of the non-desired enantiomer. If it is desired to crystallize both enantiomers separately, then a portion of new D.L.-4-hydroxyphenylglycine and sulphuric acid equivalent to the amount of sulphate that is separated with the previous crystallization may be added after warming up of the crystallization mother liquor.

After acquiring a solution it may be cooled and has to be inoculated with crystals of the other enantiomer, which thereupon crystallizes.

In the mother liquor it is possible to continue with crystallization unlimitedly.

It appeared that it is practical to make a solution of the hydrosulphate of D.L.-4-hydroxyphenylglycine at higher temperatures, for instance, at the boiling point of the solvent, of such a concentration that on cooling crystallization arises. When the crystallization starts at a higher temperature it often appears that the optical purity of the crystallized enantiomer is not 100%. It is better to crystallize below 50° C. A suitable crystallization temperature appears to lie between 0° and 40° C.

It is also possible to make a solution of the hydrosulphate of D.L.-4-hydroxyphenylglycine in a solvent with a higher dissolving power and then add a solvent in which the D.L.-4-hydroxyphenylglycine dissolves much less, through which crystallization arises.

Likewise it is possible to start in making the solution from a solvent with a higher water content and after acquiring the solution adding dry solvent, through which crystallization arises.

In the crystallization the sulphate is obtained of each enantiomer. For some applications the sulphate may be used directly. However, if the free amino-acid is needed, a simple hydrolysis may be executed in an aqueous medium using an alkali metal hydroxide, to wit NaOH and KOH or ammoniumhydroxide. Hereby the 4-hydroxyphenylglycine crystallizes and $Na_2SO_4$ dissolves.

The invention is now further elucidated by the following non-limitative examples.

EXAMPLE I

In a receiver of 100 ml are brought 60 ml of ethanol and 10.02 gr (0.06 moles) of D.L.-4-hydroxyphenylglycine and further mixed by stirring. The mixture which is obtained is then heated to 60° C. Next a solution of 6.12 gr of $H_2SO_4$ (96%) (0.06 moles) and 12 ml of water was added. After about 15 minutes stirring at 60° C. to 65° C. a solution which was so obtained was cooled to 25° C. When the temperature had reached 35° C. 0.20 gr finely divided D-(−)-4-hydroxyphenylglycine sulphate inoculation crystals were added. A slow crystallization set in. After three hours stirring at 25° C. the formed crystals were filtered and washed with 4 ml of ethanol. The filtered crystals were dried. Hereby 2.63 gr of a white crystalline substance were obtained. The specific rotation $(\alpha)$ $20_D$ was measured in an acidic medium and appeared to amount to $-119.1°$ (c=1%, 1NHCl).

Hydrolysis.

2.00 gr of the filtered and dried crystals were added with stirring to 20 ml of water. The crystals dissolved. Further it was neutralized with a 1N NaOH solution to pH 6. Hereby D.(−)-4-hydroxyphenylglycine did crystallize as a white crystalline substance. For the neutralization to pH 6 an amount of 9.1 ml 1N NaOH appeared to be necessary. From this it may be deducted that the crystals obtained during the crystallization are D.(−)-4-hydroxyphenylglycine sulphate crystals. The neutralization mixture was cooled to 0° C. and thereupon the formed crystalline product was separated by filtration. Further the product was washed on the filter with 3 ml of water and dried.

An amount of 1.39 gr of the product was obtained.

The specific rotation $(\alpha)$ $20_D$ amounted to $-154.0°$ (c=1% 1NHCl).

EXAMPLE II

In a glass receiver provided with a reflux condenser was brought while stirring 50 ml of acetone and 8.35 gr D.L.-4-hydroxyphenylglycine (0.05 moles). The obtained mixture was heated to about 50° C. Then a solution of 5.10 gr (0.05 moles) of $H_2SO_4$ (96%) and 8.25 ml of water was added. The temperature hereby rose to 56° C and the mixture started to boil. While boiling the mixture was stirred for about another 30 minutes, whereby a solution was obtained. Thereupon the solution was cooled. When a temperature of 35° C. was reached, 0.15 gr finely ground inoculation crystals of D(−)-4-hydroxyphenylglycine sulphate were added. The solution was further cooled to 18° C.

Crystallization set in. 90 minutes after the inoculation crystals were added, the formed white crystalline substance was separated by filtration and washed on the filter with 4 ml of acetone.

After drying 2.28 gr was obtained.

The specific rotation amounted to $(\alpha)$ $20_D = -119.4°$ (c=1% 1NHCl).

EXAMPLE III

The crystallization mother liquor from example II was heated stirring in a receiver of 100 ml, provided with a reflux condenser to about 50° C. Then 1.65 gr of D.L.-4-hydroxyphenylglycine (0.01 moles) and 0.48 gr of $H_2SO_4$ (96%) (0.005 moles) were added. After 20 minutes stirring while boiling (±56° C.) a solution was obtained, which was subsequently cooled to about 35° C. At this temperature 0.15 gr ground inoculation crystals of L(+)-4-hydroxyphenylglycine sulphate were added. Thereupon it was further cooled to 18° C. Crystallization set in. 70 minutes after the inoculation crystals were added, the formed crystals were separated by filtration, washed on the filter with 4 ml of acetone and dried.

2.40 gr of white crystals were obtained.

The specific rotation was measured and appeared to be: $(\alpha)$ $20_D = +121.5°$ (c=1% 1NHCl) (L(+)sulphate).

EXAMPLE IV

In a receiver of 100 ml were brought 45 ml of acetic acid and 10.02 gr D.L.-4-hydroxyphenylglycine (0.06 moles) and mixed while stirring. Then a solution of 6.13 gr of $H_2SO_4$ (96%) (0.06 moles) and 10 ml of water was added. After some minutes a solution arose. Thereupon was added 25 ml of methyl ethyl ketone in which was suspended 0.25 gr of finely ground inoculation crystals of D(−)-4-hydroxyphenylglycine sulphate. Crystallization set in. After 2 hours of stirring at 20° C. the formed crystals were filtered, washed on the filter with 5 ml of methyl ethyl ketone and then dried.

2.41 gr of crystals were obtained.

The specific rotation was $(\alpha)$ $20_D = -120.0°$ (c=1% 1NHCl).

EXAMPLE V

In a receiver of 100 ml, provided with a reflux condenser, was brought while stirring 30 ml of methanol, 30 ml of n-butanol and 10.02 gr D.L.-4-hydroxyphenylglycine (0.06 moles). The mixture which is thus obtained was heated to 50° C. and a solution of 6.12 gr of $H_2SO_4$ (96%) (0.06 moles) and 10 ml of water was added. Thereupon it was boiled for 30 minutes, whereby a solution arose. This solution was cooled to about 35° C. and there was added 0.25 gr of finely ground inoculation crystals of L-(+)-4-hydroxyphenylglycine sulphate. Then the solution was further cooled to about 20° C. Crystallization set in. 120 minutes after the inoculation crystals had been added the formed crystals were filtered, washed on the filter with 5 ml of ethanol and then dried.

2.86 gr of crystals were obtained.

On measuring the specific rotation appeared to amount to $(\alpha) 20_D = 118,8°$ (c=1% 1NHCl).

I claim:

1. A process for the preparation of D-(−)-4-hydroxyphenylglycine and L-(+)-4-hydroxyphenylglycine starting from D.L.-4-hydroxyphenylglycine, comprised of dissolving D.L.-4-hydroxyphenylglycine in a suitable solvent or a mixture of solvents at an increased temperature of 40° C. to 100° C., which solvent mixture comprises an organic solvent, 0% to 30% water $H_2SO_4$ in a molar ratio of 1:1 to the added D.L.-4-hydroxyphenylglycine, after which the solution obtained is cooled to 40° C. to 0° C. and to the cooled solution are added D-(−)-4-hydroxyphenylglycine sulphate inoculation crystals at a quantity of 2 weight percent or more of the dissolved D.L.-4-hydroxyphenylglycine for crystallizing the D-(−)-4-hydroxyphenylglycine sulphate, followed by filtering of the formed crystals, while for recovery of L-(+)-4-hydroxyphenylglycine sulphate remaining in the mother liquor is heated until 40° C. to 100° C., followed by the addition of D.L.-4-hydroxyphenylglycine and $H_2SO_4$ in water in a molar ratio of 1:0.5, after which the thus obtained solution is cooled down until 40° C. to 0° C. followed by addition of L-(+)-4-hydroxyphenylglycine sulphate inoculation crystals at a quantity of 2 weight percent or more of the dissolved D.L.-4-hydroxyphenylglycine, from which mixture after further cooling the L-(+)-4-hydroxyphenylglycine sulphate crystallizes; whereby one may also act reversely, that is first the L-(+)-4-hydroxyphenylglycine sulphate is crystallized and wherein said crystallized L-(+)-4-hydroxyphenylglycine sulphate the molar ratio of the L-(+)-4-hydroxyphenylglycine to sulphate is 2:1 and thereafter from the mother liquor the D-(−)-4-hydroxyphenylglycine sulphate and, if desired, from the formed sulphates the D-(−)-4-hydroxyphenylglycine and the L-(+)-4-hydroxyphenylglycine, respectively, may be recovered by hydrolysis making a solution of the sulphate in water at a concentration of 10% to 20% by a temperature of 20° C. to 70° C. and neutralizing the obtained solution using an aqueous solution of NaOH, KOH or $NH_4OH$ in a molar ratio of 1 mol sulphate and 2 mol of alkali and recuperating during the neutralization crystallized D(−)-4-hydroxyphenylglycine or L(+)-4-hydroxyphenylglycine by filtration.

2. The process according to claim 1 wherein the organic solvents are selected from the group consisting of carboxylic acids, alkanols, ethyleneglycolmonoalkyl ether, ketones, or combinations thereof, the solvents of the group being at least partially miscible in water.

3. The process according to claim 1 wherein the organic solvents are selected from the group consisting of formic acid, acetic acid, methanol, ethanol, propanol, butanol, ethylene glycol, acetone, methyl ethyl ketone, or combinations thereof.

4. A process according to claim 2, wherein as organic solvent acetone is used.

5. A process according to claim 2, wherein as organic solvent a mixture of methanol and n-butanol is used.

6. A process according to claims 1, 2, 3, 4 or 5, wherein the solvent mixture contains 0–30% of water.

7. A process according to claims 1, 2, 3, 4 or 5 wherein the addition of the inoculation crystals and the crystallization of the − and + hydroxyphenylglycine sulphates, respectively, is carried out at 0° C.–40° C. using 2 weight percent of more of inoculation crystals related to the dissolved quantity of D.L.-4-hydroxyphenylglycine.

8. A process according to claims 1, 2, 3, 4 or 5 wherein the hydrolysis of the − and + hydroxyphenylglycine sulphate, respectively, is carried out by addition of an alkali metal hydroxide, at 0°–40° C. in a molar ratio of 1 mol sulphate and 2 mol alkali to an aqueous solution of the mentioned sulphate, followed by filtering the obtained − and + hydroxyphenylglycine crystals, respectively.

9. The process of claim 8 wherein the alkali metal hydroxide is selected form the group consisting of NaOH, KOH, or $NH_4OH$.

* * * * *